(12) United States Patent
Sword

(10) Patent No.: US 9,625,421 B2
(45) Date of Patent: Apr. 18, 2017

(54) MANUALLY OPERATED SMALL ENVELOPE SCANNER SYSTEM

(71) Applicant: Charles Keith Sword, North Huntingdon, PA (US)

(72) Inventor: Charles Keith Sword, North Huntingdon, PA (US)

(73) Assignee: U.S. Department of Energy, Washington, DC (US)

( * ) Notice: Subject to any disclaimer, the term of this patent is extended or adjusted under 35 U.S.C. 154(b) by 415 days.

(21) Appl. No.: 14/254,058

(22) Filed: Apr. 16, 2014

(65) Prior Publication Data

US 2015/0300991 A1   Oct. 22, 2015

(51) Int. Cl.
*G01N 29/26* (2006.01)
*G01N 29/22* (2006.01)
*G01N 29/265* (2006.01)
*G01N 29/04* (2006.01)

(52) U.S. Cl.
CPC ........... *G01N 29/04* (2013.01); *G01N 29/225* (2013.01); *G01N 29/262* (2013.01); *G01N 29/265* (2013.01); *G01N 2291/106* (2013.01)

(58) Field of Classification Search
CPC .... G01N 29/04; G01N 29/225; G01N 29/265; G01N 27/90; G01N 2291/106
USPC ......................................................... 73/618
See application file for complete search history.

(56) References Cited

U.S. PATENT DOCUMENTS

| | | | | |
|---|---|---|---|---|
| 4,352,984 A * | 10/1982 | Ohara | ..................... | H04N 1/053 250/201.1 |
| 5,912,458 A * | 6/1999 | Squires | ................ | H04N 1/0607 250/234 |
| 6,509,969 B1 * | 1/2003 | Takeshita | ............... | G01C 19/00 250/234 |
| 2004/0239318 A1 * | 12/2004 | Xiao | ...................... | B82Y 35/00 324/244 |
| 2006/0201252 A1 * | 9/2006 | Georgeson | ........... | G01N 29/041 73/641 |
| 2006/0243051 A1 * | 11/2006 | Bui | ...................... | G01N 29/043 73/618 |

* cited by examiner

*Primary Examiner* — J M Saint Surin
(74) *Attorney, Agent, or Firm* — Jennifer R. Mahalingappa; Robert T. Burns; Brian J. Lally

(57) ABSTRACT

A scanner system and method for acquisition of position-based ultrasonic inspection data are described. The scanner system includes an inspection probe and a first non-contact linear encoder having a first sensor and a first scale to track inspection probe position. The first sensor is positioned to maintain a continuous non-contact interface between the first sensor and the first scale and to maintain a continuous alignment of the first sensor with the inspection probe. The scanner system may be used to acquire two-dimensional inspection probe position data by including a second non-contact linear encoder having a second sensor and a second scale, the second sensor positioned to maintain a continuous non-contact interface between the second sensor and the second scale and to maintain a continuous alignment of the second sensor with the first sensor.

20 Claims, 11 Drawing Sheets

MANUALLY OPERATED SMALL ENVELOPE SCANNER SYSTEM

STATEMENT REGARDING FEDERALLY SPONSORED RESEARCH AND DEVELOPMENT

This invention was made with government support under DE-AC11-98PN38206 awarded by the United States Department of Energy. The government has certain rights in the invention.

BACKGROUND

1. Field

Embodiments of the invention discussed herein relate to a scanner system and method for acquisition of inspection data using ultrasonic inspection or eddy current inspection methods.

2. Description of the Related Art

In destructive testing, defects are made apparent by stressing the object, for example, by bending or applying tension until any cracks present on the object break open. By comparison, nondestructive testing methods apply forces at such a low intensity that the object does not become damaged. Two such nondestructive testing methods that are relevant to the embodiments of the invention disclosed herein include ultrasonic inspection and eddy current inspection methods.

Ultrasonic inspection is carried out using an ultrasonic inspection probe and a scanner for tracking probe position, such that ultrasonic inspection data (e.g., waveforms representative of internal cracks or flaws, object thickness, etc.) generated by the ultrasonic inspection probe may be correlated with position data generated by the scanner and displayed to the operator and/or recorded for future use. Conventional ultrasonic inspection probes utilize a single transducer that transmits ultrasonic waves in a single, fixed direction. As a result, conventional ultrasonic inspection probes must be moved between each point in an inspection area and, consequently, are generally used with scanners capable of moving along two axes (i.e., x-axis and y-axis). Phased array ultrasonic inspection probes utilize multiple transducers which are pulsed individually by a controller such that the inspection probes can transmit a beam of ultrasonic waves into the object at various angles. As a result, phased array ultrasonic inspection probes can be used to inspect broad segments of an inspection area without being moved and are effective when used with scanners capable of movement along only one axis.

Like ultrasonic inspection, eddy current inspection is carried out using an inspection probe and a scanner for tracking probe position. Eddy current inspection probes utilize an excitation coil powered by alternating current to generate electric currents (eddy currents) in the object being inspected and a receiver coil to monitor variations in the resulting eddy currents. Eddy current inspection data (e.g., variations in the eddy currents representative of variations in composition or the presence of internal cracks or flaws) are then correlated with position data generated by the scanner and displayed to the operator and/or recorded for future use. Eddy current inspection probes, like conventional ultrasonic inspection probes, may be used with scanners capable of moving along two axes (i.e., x-axis and y-axis).

Existing scanners include a motor driven carriage fixed to a track that is mounted to the circumference of the object being inspected. The motor driven carriage is attached to the inspection probe and the inspection probe's position is tracked using the motor's controller or a rotary encoder that is mechanically coupled to gear teeth machined in the track. For conventional ultrasonic inspection and eddy current inspection, where scanners capable of movement along two axes are generally used, a second track, configured perpendicular to the first track, is fixed to the motor driven carriage.

Existing scanners are complex and have many interacting mechanical parts. As a result, they are costly to construct and require frequent repair and maintenance. The cost to develop and deploy these existing scanners has led to the deferment of ultrasonic inspection of thermal sleeves. Thermal sleeves are typically installed on pipes in locations where rapid changes in the temperature of water flowing in the pipes may cause fatigue cracks to grow. Occluded regions on the internal surfaces of thermal sleeves are susceptible to stress corrosion cracking. While it would be prudent to regularly inspect thermal sleeves to verify that stress corrosion cracking has not propagated, such inspection has been deferred until a lower cost scanner is available.

In addition, existing scanners require a minimum axial clearance of 7 inches to locate the track and motor. The large axial clearance required to locate existing scanners led to the deferment of inspection of certain welds in 14-inch, stainless steel piping that were required to be inspected as part of an in-service inspection program.

Two other existing scanners, which function differently than the above-mentioned scanners, include the Bettis "Free Motion Scanner" and Bettis "Orientation-Sensed Scanner." The Free Motion Scanner is a hand-operated ultrasonic inspection device that may be moved over a complex object in an arbitrary pattern to generate an image of the object. The Free Motion Scanner is primarily intended for use in inspecting objects with complex surface contours, not objects such as pipes that have simple surface contours. See U.S. Pat. No. 6,122,967, which is hereby incorporated by reference. The Orientation Sensed Scanner is a single-axis scanner that senses the inclination of the probe as it is scanned, in contrast to existing scanners that sense the linear motion around the circumference of an object. However, current embodiments of the Orientation Sensed Scanner are not compatible with certain phased array ultrasonic inspection probes.

In light of the foregoing, there is a continuing need for cheaper, simpler scanners that can be used to carry out image inspection of an object, including ultrasonic inspection and eddy current inspection, within a small space envelope.

BRIEF SUMMARY

To solve the above and/or other problems, it is an aspect of the described embodiments to provide a system including an inspection probe and a first non-contact linear encoder having a first sensor and a first scale, the first sensor positioned to maintain a continuous non-contact interface between the first sensor and the first scale and to maintain a continuous alignment of the first sensor with the inspection probe.

To solve the above and/or other problems, it is an aspect of the described embodiments to provide a method including using an embodiment of the scanner system having an inspection probe and a first non-contact linear encoder including a first sensor and a first scale, the method including generating a signal representative of a position of the inspection probe by moving the first sensor along the first scale while maintaining a continuous non-contact interface between the first sensor and the first scale and maintaining a continuous alignment of the first sensor with the inspection probe.

To solve the above and/or other problems, it is an aspect of the described embodiments to provide a method including using a scanner system having an inspection probe and first and second non-contact linear encoders, the first non-contact linear encoder including a first sensor and a first scale and the second non-contact linear encoder including a second sensor and a second scale, the method including generating a signal representative of a position of the inspection probe on a first axis by moving the first sensor along the first scale on the first axis while maintaining a continuous non-contact interface between the first sensor and the first scale and maintaining a continuous alignment of the first sensor with the inspection probe; and generating a signal representative of a position of the inspection probe on a second axis by moving the second sensor along the second scale on the second axis while maintaining a continuous non-contact interface between the second sensor and the second scale and maintaining a continuous alignment of the second sensor with the first sensor.

Additional aspects and/or advantages will be set forth in part in the description which follows and, in part, will be obvious from the description, or may be learned by practice of the invention.

BRIEF DESCRIPTION OF THE SEVERAL VIEWS OF THE DRAWINGS

These and/or other aspects and advantages will become more readily appreciated from the following description of embodiments, taken in conjunction with the accompanying drawings in which.

DETAILED DESCRIPTION

Figure 1:
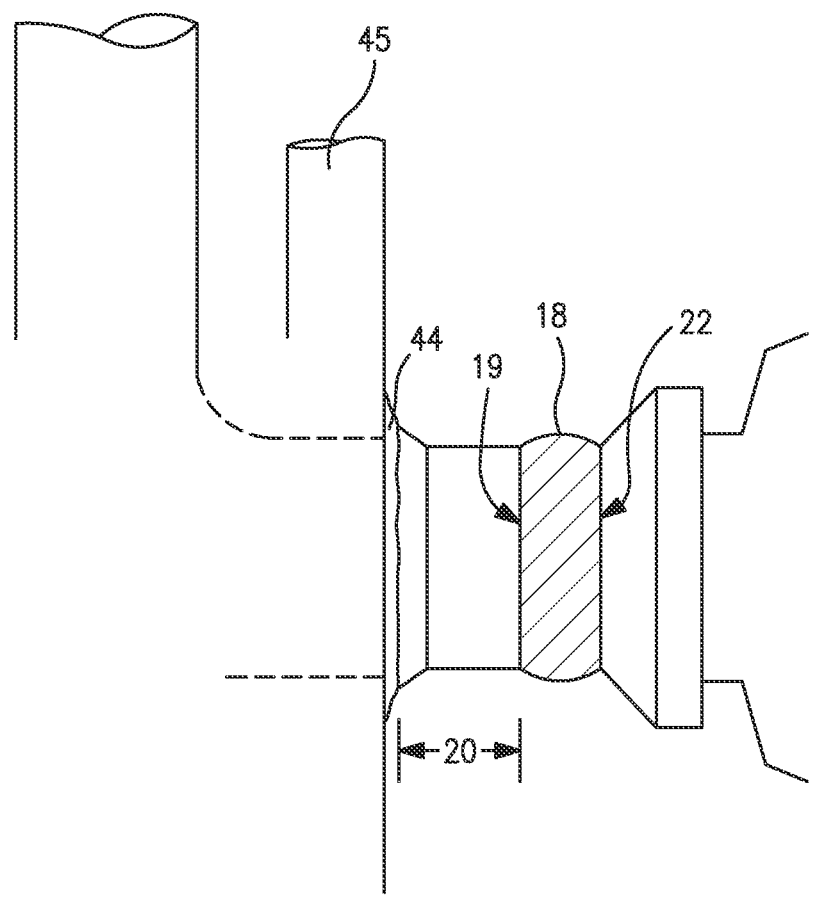
FIG. 1 is an illustration of a weld in 14-inch, stainless steel pipe having a small access limitation.

Embodiments are described below, examples of which are illustrated in the accompanying drawings, wherein like reference numerals refer to the like elements throughout. Although a few embodiments have been shown and described, those skilled in the art will appreciate that changes may be made in these embodiments without departing from the principles and spirit of the invention, the scope of which is defined in the appended claims and their equivalents.

Figure 2:
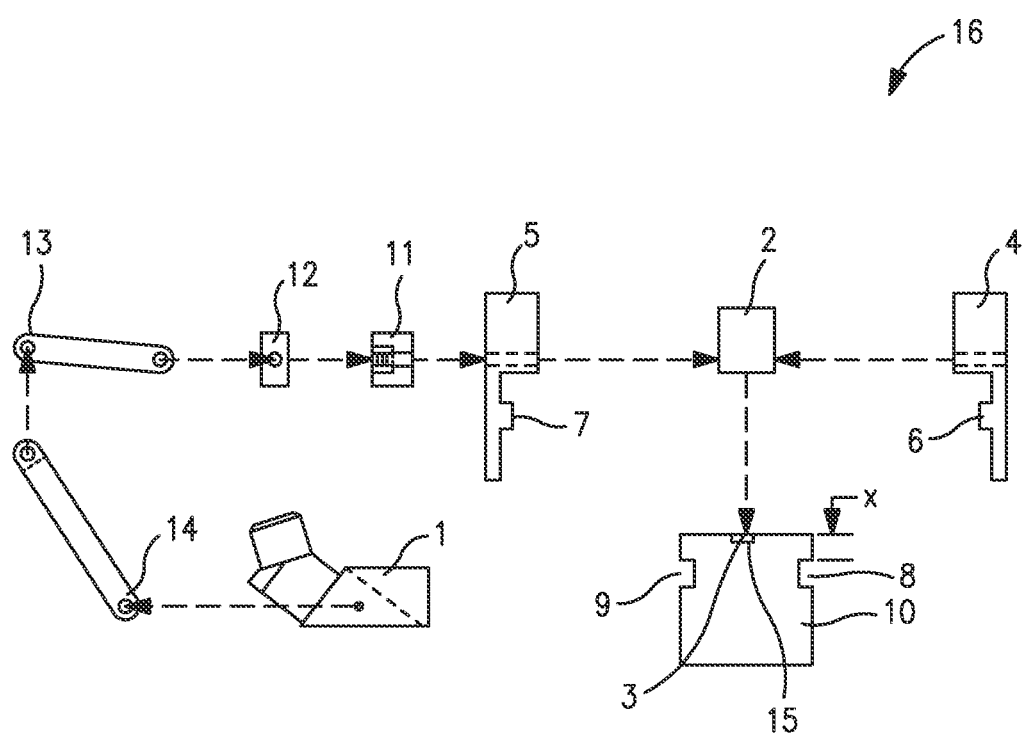
FIG. 2 is an illustration from an exploded view of an embodiment of the scanner system that allows movement along a single axis ("single-axis scanner system").

Embodiments of the invention disclosed herein relate to a manually operated, small envelope scanner system and method for image inspection of an object. Embodiments of the scanner system disclosed herein (see, e.g., FIG. 2) include an inspection probe 1 and a first non-contact linear encoder having a first sensor 2 and a first scale 3. The inspection probe 1 may be a phased array ultrasonic inspection probe, a conventional ultrasonic inspection probe, or an eddy current inspection probe. The first non-contact linear encoder may be a magnetic non-contact linear encoder or an optical non-contact linear encoder. The scale of a magnetic non-contact linear encoder is imprinted with a fine grid of magnetic fields. When the sensor of a magnetic non-contact linear encoder is moved along the scale, the sensor measures the alternating magnetic fields on the scale and converts the measurements into a signal representative of a position of the sensor (or of a movement of the sensor, which may be converted to a position of the sensor). The scale of an optical non-contact linear encoder has a fine grid etched on its surface. When the sensor of an optical non-contact linear encoder is moved along the scale, the sensor transmits light onto the scale, measures fluctuations in light reflected from the scale, and converts the measurements into a signal representative of a position of the sensor (or of a movement of the sensor, which may be converted to a position of the sensor).

Magnetic non-contact linear encoders may provide benefits that are not provided by optical non-contact linear encoders when included in embodiments of the scanner system. First, a magnetic non-contact linear encoder has greater tolerances for misalignment between the sensor and the scale than an optical non-contact linear encoder. Second, a magnetic non-contact linear encoder, unlike an optical non-contact linear encoder, is not affected by the presence of oil or water on the surface of the scale. Finally, a protective foil may be placed over an active surface of the scale (the surface facing the sensor) of a magnetic non-contact linear encoder during inspection to protect the scale from wear and tear, thereby potentially extending the useful lifetime of the scale (the magnetic non-contact linear encoder will not be adversely affected by the presence of protective foil, or by the presence of large magnetic steel components or weak external magnetic fields).

Single-Axis Scanner System

An embodiment of a single-axis scanner system 16 is depicted in FIGS. 2-5. The embodiment includes the inspection probe 1 and the first non-contact linear encoder having the first sensor 2 and the first scale 3. The first sensor 2 is positioned to maintain a continuous non-contact interface between the first sensor 2 and the first scale 3 and to maintain a continuous alignment of the first sensor 2 with the inspection probe 1. As the first sensor 2 is moved along the first scale 3, causing the first sensor 2 to read the first scale 3, the first sensor 2 generates a signal representative of a position of the first sensor 2. Because the inspection probe 1 is maintained in a continuous alignment with the first sensor 2, the signal representative of a position of the first sensor 2 also constitutes a signal representative of a position of the inspection probe 1 along a given axis. The signal representative of a position of the inspection probe 1 may be correlated with the signal representative of an image of an object 17, which is generated by the inspection probe 1. The resulting position-based inspection data may be viewed on a display (not shown) by an operator and/or stored for later use.

In addition to the inspection probe 1 and the first non-contact linear encoder, the embodiment depicted in FIGS. 2-5 includes a first track 10, a first carriage 28, and a probe mount 29. The first track 10 is machined in a semi-circular shape so that it may be affixed securely to the object 17 being inspected, which may be a 14-inch stainless steel pipe having a longitudinal axis and a weld 18 having a weld toe 19. The first track 10 has a longitudinal axis and first, second, and third grooves 8, 9, 15, the first groove 8 being located in a right side surface of the first track 10, the second groove 9 being located in a left side surface of the first track 10, and the third groove 15 being located in a top surface of the first track 10. When affixed to the object 17, the first track 10 is aligned such that the longitudinal axis of the first track 10 is perpendicular to the longitudinal axis of the object 17. The first scale 3 is embedded in the third groove 15 to maintain its position on the first track 10. One or more carriage stops (not shown) may be attached to each end of the first scale 3 to prevent the ends of the first scale 3 from peeling off of the first track 10 and to prevent the first carriage 28 from sliding off of an end of the first track 10.

The first carriage 28 includes a first right half carriage 4 and first left half carriage 5 (though the first carriage may include a single body or more than two components (not shown)). The first right half carriage 4 is affixed to the first left half carriage 5 by two appropriate length screws 27. The two appropriate length screws 27 are run through two threaded through holes in the first sensor 2 to affix the first sensor 2 to the first right half carriage 4 and to the first left half carriage 5 (the first sensor may be affixed to the first carriage 28 in other ways as well, including by use of an adhesive or by placing the first sensor 2 in a compartment (not shown) in the first carriage 28 that is sized to securely house the first sensor 2). A handle 30 may be included on either half of the first carriage 28 to facilitate the operator's ability to move the first carriage 28 along the first track 10.

Figure 4:
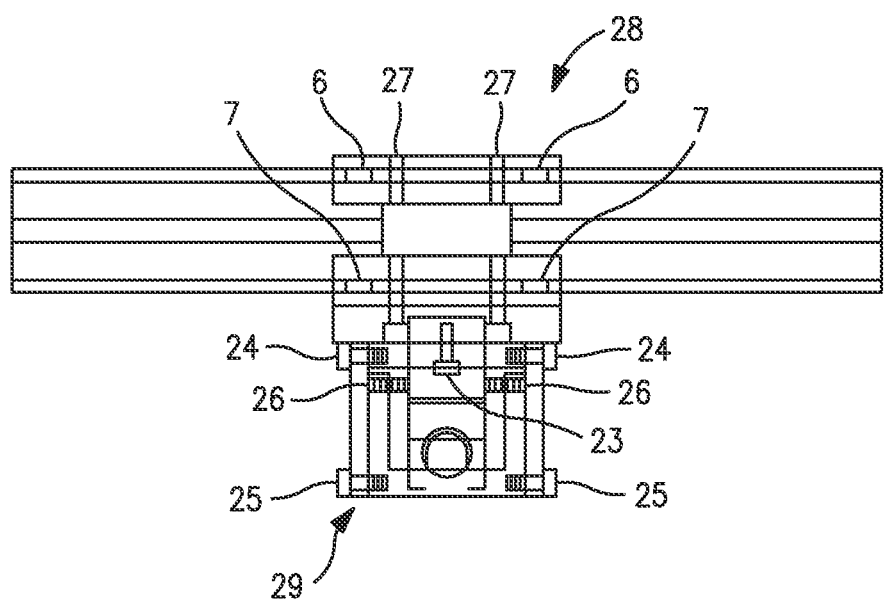
FIG. 4 is an illustration from a top view of an embodiment of the single-axis scanner system of FIG. 2.

The first carriage 28 (in this embodiment, the conjoined first right half carriage 4 and first left half carriage 5) is connected to the first track 10 by the interaction of first and second connecting members 6, 7 with the first and second grooves 8, 9, respectively. Although FIG. 4 illustrates the use of tangs as the first and second connecting members 6, 7, this is for illustrative purposes only, and other elements (i.e., roller bearings, curved slabs, etc.) may be used for the first and second connecting members 6, 7. The first connecting member 6 is located on the first right half carriage 4 and the second connecting member 7 is located on the first left half carriage 5. The first and second connecting members 6, 7 fit within the first and second grooves 8, 9, respectively, to maintain a position of the first carriage 28 relative to the first track 10, whether the first carriage 28 is at rest or being moved along the first track 10.

The location of the first and second grooves 8, 9 with respect to the top surface (dimension x in FIG. 2) of the first track 10 is varied according to the diameter of the object being inspected. The location of the first and second grooves 8, 9, as well as the depth of the third groove 15, is determined to ensure that the distance from the active point of the first sensor 2 to the first scale 3 is maintained within the tolerance required for the specific first sensor 2 used (i.e., to ensure that a continuous, non-contact interface is maintained between the first sensor 2 and the first scale 3). Alignment (roll, pitch, and yaw) of the first sensor 2 with respect to the first track 10 may be maintained by standardizing the width of the first track 10 and the dimensions of the first carriage 28.

The probe mount 29 includes a probe mount base 11, a probe mount pivot 12, first and second probe mount links 13, first and second probe mount yokes 14, and seven shoulder screws 23-26. The probe mount base 11 is affixed to the first left half carriage 5 with two appropriate length screws 27 that also affix the first left half carriage 5 and first right half carriage 4 to each other as well as to the first sensor 2, as discussed above. The probe mount pivot 12 is connected to the probe mount base 11 with a centrally located shoulder screw 23. The first and second probe mount links 13 are connected to the probe mount pivot 12 with two shoulder screws 24. Likewise, the first and second probe mount yokes 14 are connected to the first and second probe mount links 13, respectively, with two shoulder screws 25. Finally, the first and second probe mount yokes 14 are connected to the inspection probe 1 using two shoulder screws 26. The probe mount 29 may provide a benefit of allowing an active surface of the inspection probe 1 to maintain a continuous point of contact 21 with the object 17.

The first and second probe mount links 13 are of a length such that the furthest axial position of the probe mount 29 from the weld toe 19 is, for example, 1.875 inches (the length of the first and second probe mount links 13 may be varied for the particular inspection application). Therefore, it is an aspect of the embodiment of the single-axis scanner system 16 depicted in FIGS. 2-5 to be capable of being used to inspect the type of weld 18 depicted in FIG. 1. This weld 18 provides as little as 2.125 inches of axial clearance (i.e., allows clearance for a scanner system having a space envelope 20 of only 2.125 inches) between the weld toe 19 and lagging 44 protruding from a shield wall 45, and has an opposite weld toe 22 that is a valve body having a non-uniform contour. Due to the installed location of the weld 18, it likely could not be inspected using existing scanner systems.

Figure 6:
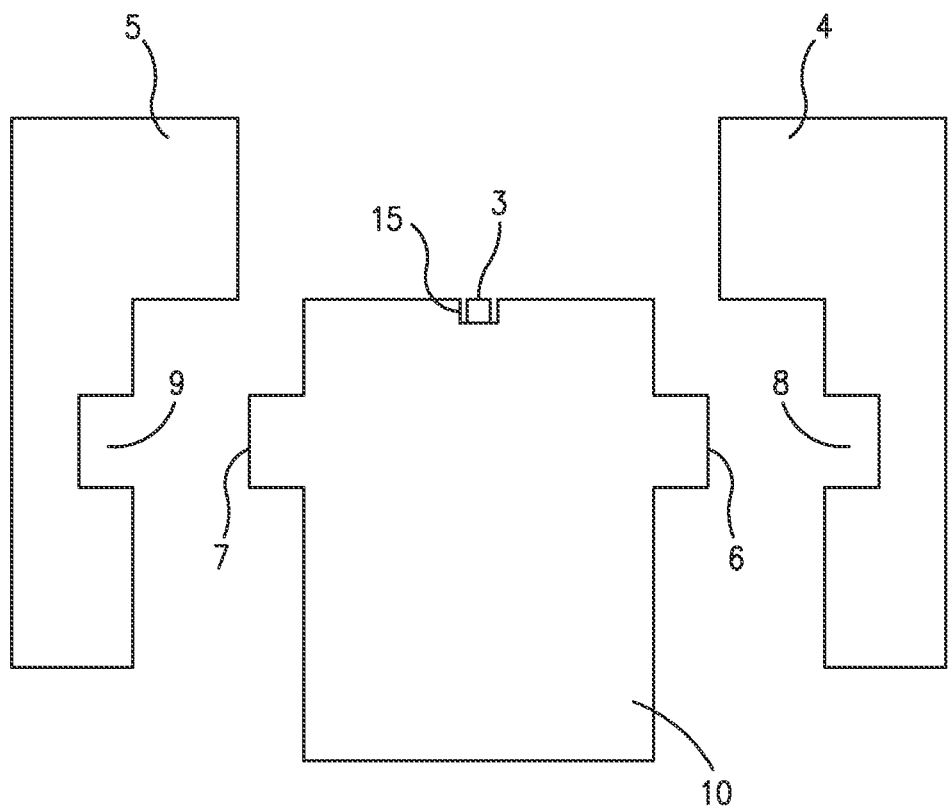
FIG. 6 is an illustration of a first carriage of FIG. 2 having first and second grooves and a first track of FIG. 2 having corresponding first and second connecting members, respectively.
Figure 7:
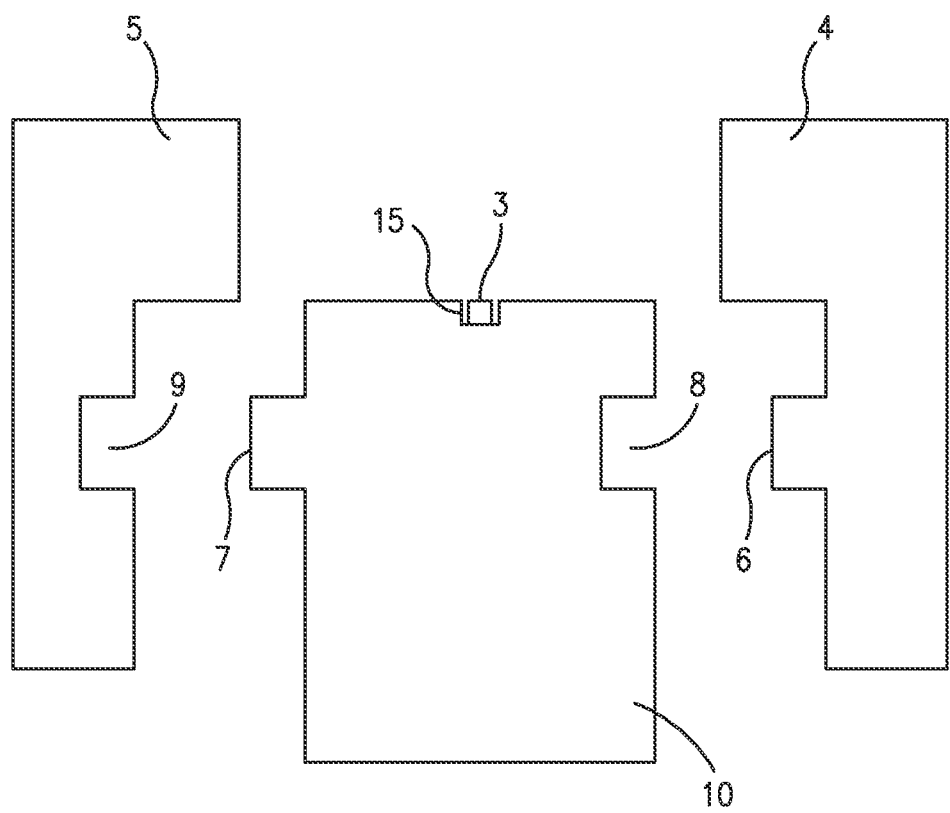
FIG. 7 is an illustration of a first carriage of FIG. 2 having a first connecting member and a second groove, and a first track of FIG. 2 having a corresponding first groove and second connecting member, respectively.

FIGS. 6-7 depict two additional examples of how the first carriage 28 and first track 10 may be configured to have first and second connecting members 6, 7 that fit into first and second grooves 8, 9. In FIG. 6, the first connecting member 6 is located on the right side surface of the first track 10 and the second connecting member 7 is located on the left side surface of the first track 10. The first groove 8 is located in the first right half carriage 4 and the second groove 9 is located in the first left half carriage 5. In FIG. 7, the first connecting member 6 is located on the first right half carriage 4 and the second connecting member 7 is located on the left side surface of the first track 10. The first groove 8 is located in the right side surface of the first track 10 and the second groove 9 is located in the first left half carriage 5.

Example 1

A specific example of the general single-axis scanner system 16 depicted in FIGS. 2-5 will now be described. In this example, the single-axis scanner system 16 was used to carry out inspection of a weld 18 in an object 17 (specifically, a 14-inch pipe 17). The inspection probe 1 used in the single-axis scanner system 16 may be a commercially available phased array ultrasonic inspection probe having a pulse counter. The first non-contact linear encoder used in the single-axis scanner system 16 was a magnetic non-contact linear encoder, available from RENISHAW®, that when powered with a 5 volt (direct current) supply outputs a transistor-transistor logic (TTL) signal in a differential quadrature format, providing a quadrature count that may be correlated to real-time position of the first sensor 2 (as well as the position of the inspection probe 1, because of the continuous alignment maintained between the first sensor 2 and the inspection probe 1) using a compatible increment/decrement counter.

Figure 3:
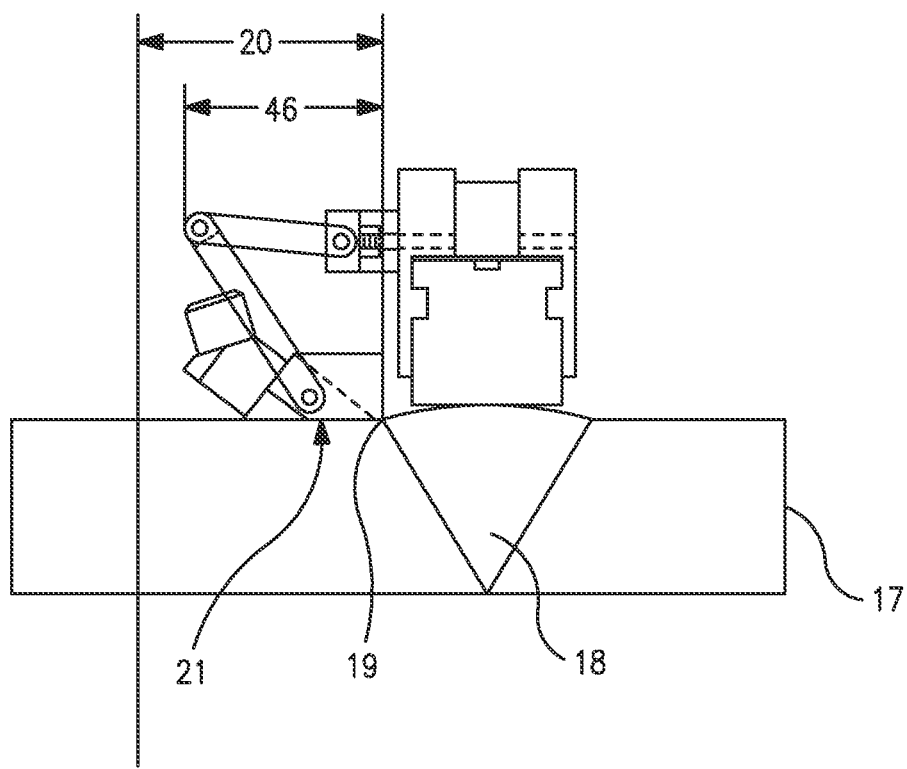
FIG. 3 is an illustration from a front view of an embodiment of the single-axis scanner system of FIG. 2.
Figure 5:
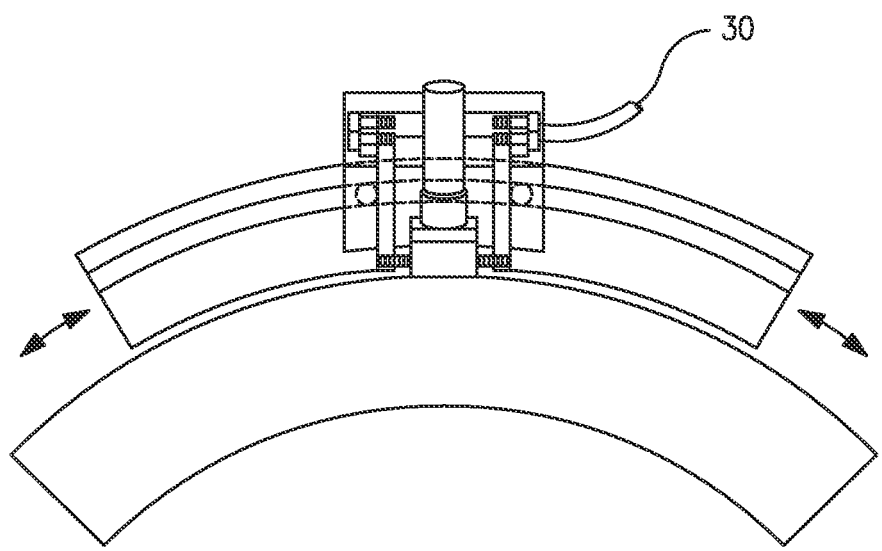
FIG. 5 is an illustration from a side view of an embodiment of the single-axis scanner system of FIG. 2.

FIGS. 3-5 depict the different views of the single-axis scanner system 16 mounted on the weld 18 in the 14-inch pipe 17. The first scale 3 was positioned in the third groove 15 in the top surface of the first track 10 and covered with a protective foil (not shown). The first track 10 was machined in a semi-circular shape and strapped to the surface of the pipe 17 using a ratcheted tie down (not shown). The full circumference of the weld 18 was inspected by scanning 120 degree sections of the pipe 17, loosening the ratcheted tie down, and moving the single-axis scanner system 16 between scans carried out with the phased array ultrasonic inspection probe. With the front face of the inspection probe 1 positioned at a toe of the weld 18, the maximum axial extent 46 of the single-axis scanner system 16 was 1.875 inches from the weld toe 19, thus demonstrating that the single-axis scanner system 16 fit within a space envelope 20 of 2.125 inches from the weld toe 19.

Figure 9A:
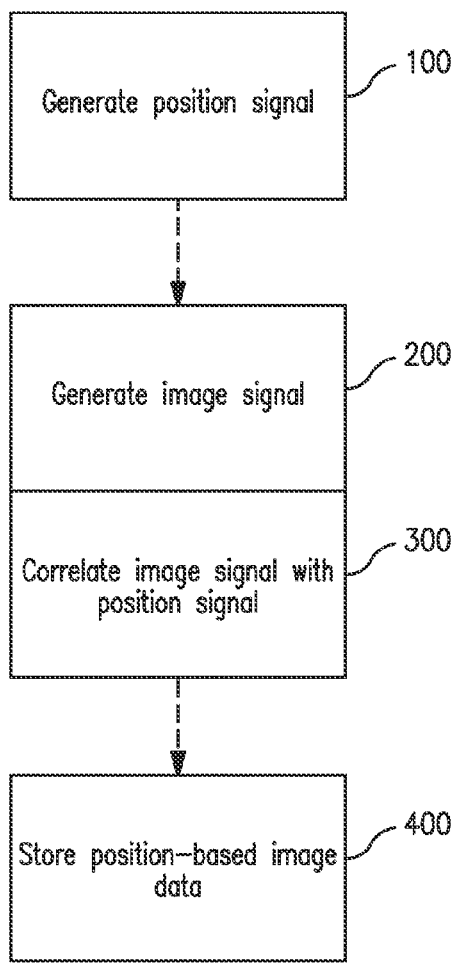
FIG. 9A is a flowchart of an embodiment of a method for image inspection of an object using an embodiment of the single-axis scanner system of FIG. 2.

As the first sensor 2 was moved along the first scale 3, the first sensor 2 output a quadrature signal that was input into the pulse counter of the phased array ultrasonic inspection probe (as in FIG. 9A). The phased array delay laws of the inspection probe 1 were implemented to electronically sweep an ultrasonic beam between 35 and 75 degrees as the inspection probe 1 was scanned around the circumference of the weld. The position feedback provided by the first sensor 2 to the inspection probe 1 enabled position-based inspection data to be stored in a personal computer and analyzed with appropriate software.

In addition, the embodiment of the single-axis scanner system discussed in this example was qualified in accordance with standard industry practice. The standard industry practice in ultrasonic inspection scanner system development is to conduct a qualification test in which the capability of the scanner system is demonstrated using mockup specimens having a range of known flaws. The scanner system is judged to be qualified if a sufficient number of the flaws are found when operators conducting the test have little or no a-priori knowledge of the number and location of the flaws.

Figure 11:
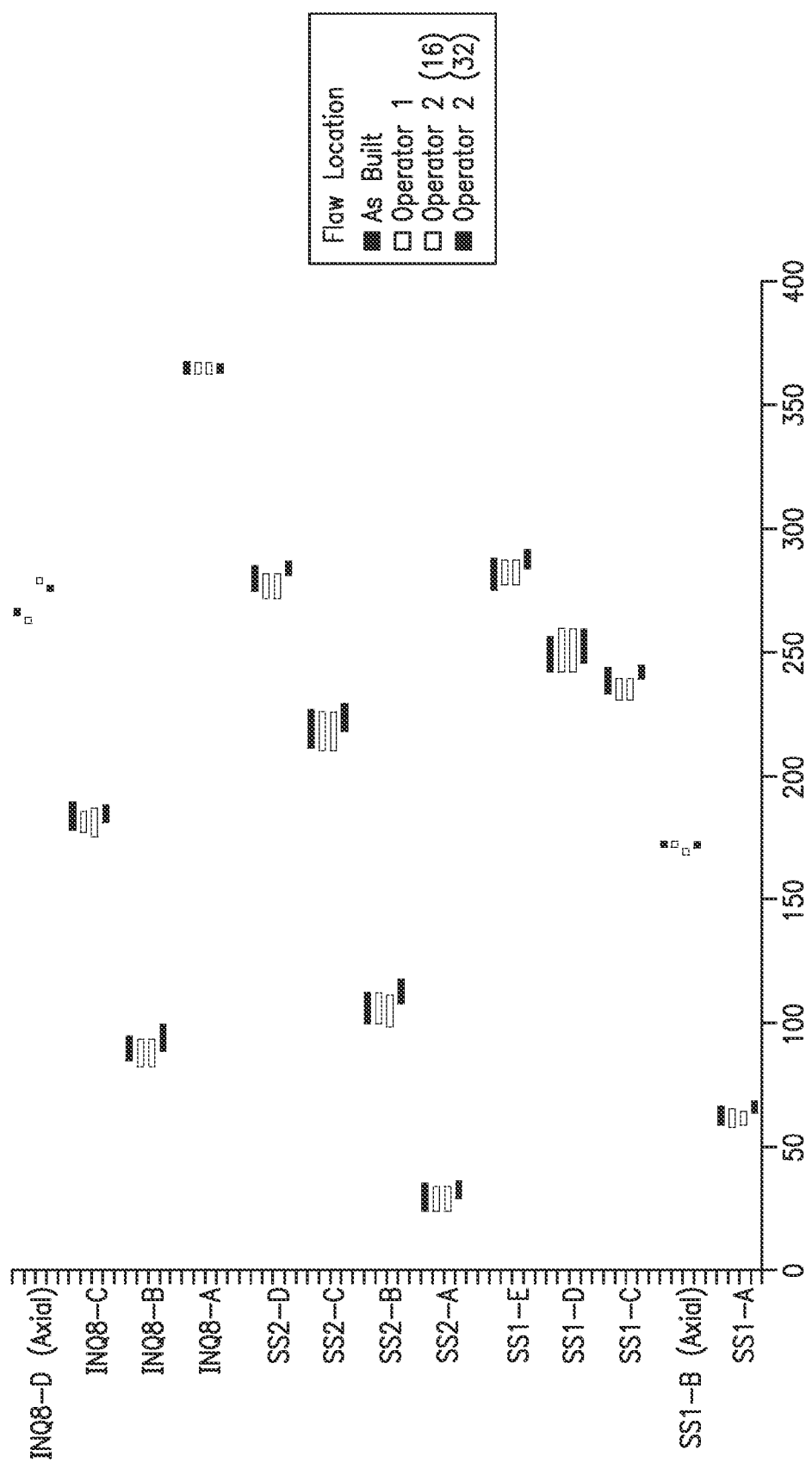
FIG. 11 is a graph depicting the results of detection qualification tests performed using an embodiment of the method for image inspection of an object of FIG. 9A using an embodiment of the single-axis scanner system of FIG. 2.

FIG. 11 shows the results of the qualification tests. The operators that carried out the qualifications test identified 13 of the 13 flaws present in the mockup specimens. These results exceed the standard industry requirements for qualification.

Example 2

Another specific example of the general single-axis scanner system 16 depicted in FIGS. 2-5 will now be described. In this example, four single-axis scanner systems 16 were used to carry out inspection of thermal sleeves on four different piping sizes, each requiring a unique single-axis scanner system 16. The single-axis scanner systems 16 used to carry out the inspections were substantially similar to the single-axis scanner system 16 depicted in FIGS. 2-5 and described above. The inspection probe 1 used in the single-axis scanner system 16 was a commercially available phased array ultrasonic inspection probe. The first non-contact linear encoder was (as in Example 1) a magnetic non-contact linear encoder available from RENISHAW®. Two substantive differences between the single-axis scanner system 16 depicted in FIGS. 2-5 and the single-axis scanner systems 16 developed to carry out inspection of thermal sleeves were that the first tracks 10 used in the four single-axis scanner systems 16 were machined to conform to the shape and dimensions of the four different sizes of thermal sleeves (rather than to conform to the shape of a 14-inch pipe) and the first and second probe mount links 13 were fabricated at lengths appropriate for the four different sizes of thermal sleeves (rather than at lengths appropriate for inspection of 14-inch pipe). The four single-axis scanner systems 16 were designed and fabricated in less than two months at a cost of less than $16,000.

Two-Axis Scanner System

Embodiments of a two-axis scanner system 43 (see, e.g., FIG. 8) include an inspection probe 1' and first and second non-contact linear encoders, the first non-contact linear encoder having a first sensor 2' and a first scale 3' and the second non-contact linear encoder having a second sensor 32 and a second scale 33. The first sensor 2' is positioned to maintain a continuous non-contact interface between the first sensor 2' and the first scale 3' and to maintain a continuous alignment of the first sensor 2' with the inspection probe 1'. The second sensor 32 is positioned to maintain a continuous non-contact interface between the second sensor 32 and the second scale 33 and to maintain a continuous alignment of the second sensor 32 with the first sensor 2'. As the first and second sensors 2', 32 are moved along the first and second scales 3', 33, respectively, the first sensor 2' generates a signal representative of a position of the inspection probe 1' on a first axis (i.e., x-axis) and the second sensor 32 generates a signal representative of a position of the second sensor 32 on a second axis (i.e., y-axis). Because the second sensor 32 is maintained in a continuous alignment with the first sensor 2', which itself is maintained in a continuous alignment with the inspection probe 1 (this alignment being perpendicular to the continuous alignment of the second sensor 32 with the first sensor 2'), the signal representative of a position of the second sensor 32 along the second axis also constitutes a signal representative of a position of the inspection probe 1' along the second axis. The signals representative of a position of the inspection probe 1' on the first axis and the second axis i.e., x-y axis position data) may be correlated with the signal representative of an image of the object 17', a one-inch pipe having a weld 18, which is generated by the inspection probe 1'.

Figure 8:
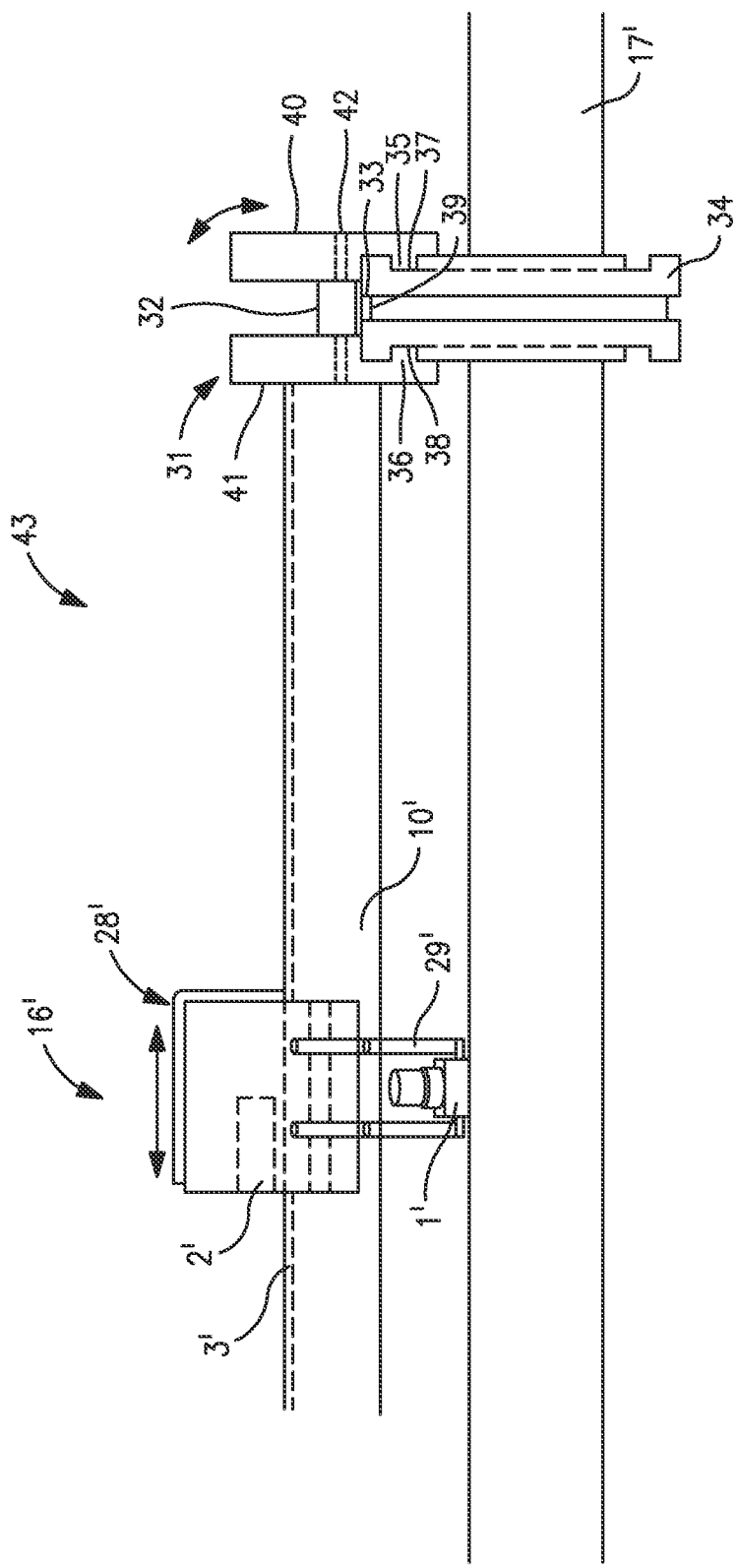
FIG. 8 is an illustration of an embodiment of the scanner system that allows movement along two axes ("two-axis scanner system").

An embodiment of the two-axis scanner system 43 is depicted in FIG. 8. The embodiment illustrated includes a single-axis scanner system 16', a second track 34, a second carriage 31, and the second non-contact linear encoder including the second sensor 32 and a second scale 33. The single-axis scanner system 16' is substantially similar to that depicted in FIGS. 2-5 and described above (having components including but not limited to an inspection probe 1', a first non-contact linear encoder having a first sensor 2' and a first scale 3', a first carriage 28', a first track 10' having a longitudinal axis, and a probe mount 29'). The probe mount 29' of the single-axis scanner system 16' extends an appropriate distance from the first carriage 28' so that a continuous point of contact 21' may be maintained between an active surface of the inspection probe 1' and the object 17' being inspected.

The second track 34 has a longitudinal axis and fourth, fifth, and sixth grooves 37-39 that extend along the length of the second track 34. The fourth groove 37 is located on a right side surface of the second track 34, the fifth groove 38 is located on a left side surface of the second track 34, and the sixth groove 39 is located on a top surface of the second track 34. The second carriage 31 includes a second right half carriage 40 having a third connecting member 35 and a second left half carriage 41 having a fourth connecting member 36.

The configuration of the second track 34, second carriage 31, second sensor 32, and second scale 33 is substantially similar to the configuration of the single-axis scanner system 16'. The second scale 33 is positioned in the sixth groove 39, which is machined in the top of the second track 34. The second sensor 32 is affixed to the second carriage 31 by two appropriate length shoulder screws 42, which pass through two threaded through holes in the second sensor 32 as well as the second right half carriage 40 and second left half carriage 41. The second carriage 31 is connected to and moveable along the second track 34 to maintain a continuous non-contact interface between the second sensor 32 and the second scale 33 and to maintain a continuous alignment of the second sensor 32 with the first sensor 2'. The second carriage 31 is connected to the second track 34 by the interaction of the third connecting member 35 (e.g., two tangs or two roller bearings) with the fourth groove 37 and the interaction of the fourth connecting member 36 (e.g., two tangs or two roller bearings) with the fifth groove 38.

Example 3

A specific example of the general two-axis scanner system 43 depicted in FIG. 8 will now be described. In this example, a two-axis scanner system 43 was used to investigate initiation and growth of fatigue cracks in welds in one-inch pipe 17'. The two-axis scanner system 43 used to carry out the inspections is depicted in FIG. 8 and described above (the third connecting member 35 being two tangs and the fourth connecting member 36 being two tangs). The inspection probe 1 used in the two-axis scanner system 43 was a commercially available conventional ultrasonic inspection probe. The first and second non-contact linear encoders used in the two-axis scanner system 43 were (as in Example 1 and Example 2) magnetic non-contact linear encoders available from RENISHAW®.

The embodiment of the two-axis scanner system 43 disclosed herein was used to periodically inspect welds in one-inch pipe to identify the initiation and location of cracks and to monitor their growth until they are near breakthrough of the pipe wall. It was important that the ultrasonic inspection data collected using this embodiment be recorded at each stage of inspection such that the growth between inspections could be tracked. Further, existing scanner systems proved impractical for the inspection of these welds because of their large size and footprint relative the two-axis scanner system 43 disclosed herein. The two-axis scanner system 43 was designed and fabricated in less than two months at a cost of less than $6,000.

Method Using Single-Axis Scanner System

Figure 9B:
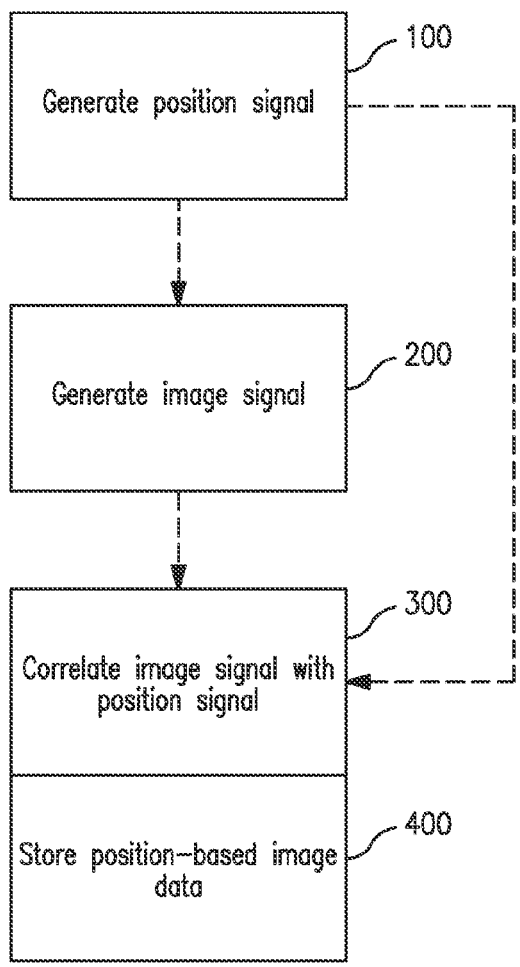
FIG. 9B is a flowchart of a second embodiment of the method for image inspection of an object using an embodiment of the single-axis scanner system of FIG. 2.

Embodiments of the method for image inspection of an object using a single-axis scanner system (e.g., a scanner system including an inspection probe and a first non-contact linear encoder having a first sensor and a first scale, the first sensor positioned to maintain a continuous non-contact interface between the first sensor and the first scale and to maintain a continuous alignment of the first sensor with the inspection probe) include four operations 100, 200, 300, and 400 (as depicted in FIGS. 9A and 9B). The first operation 100 includes generating a signal representative of a position of the inspection probe on a first axis. The first operation 100 may be carried out by connecting the first sensor to an appropriate power supply and ensuring that the first sensor is prepared to read the first scale. The first sensor may then be moved along the first scale by an operator while a continuous non-contact interface is maintained between the first sensor and the first scale, such that the first sensor is able to read the first scale.

The second operation 200 includes generating a signal representative of an image of the object using the inspection probe. The inspection probe is positioned such that a continuous point of contact is present between an active surface of the inspection probe and the surface of the object being inspected. The inspection probe is connected to an appropriate power supply and made to scan the object. The inspection probe may then be moved simultaneously with any movement of the first sensor, such that a continuous alignment is maintained between the first sensor and the inspection probe.

The third operation 300 includes correlating the signal representative of a position of the inspection probe with the signal representative of an image of the object. The signal representative of a position of the inspection probe may be input directly into the inspection probe, as depicted in FIG. 9A, if the inspection probe is compatible with the signal. Alternatively, the signal may be input into a computer (not shown) having appropriate software, as depicted in FIG. 9B.

The fourth operation 400 includes storing position-based image data obtained from the previous three operations 100, 200, 300 using the computer. The position-based image data stored on the computer may be displayed to an operator and/or analyzed for other purposes using appropriate software (e.g., comparing images taken of a single inspection location over time to track the development of cracks and/or a decrease in pipe wall thickness).

When the single-axis scanner system used in an embodiment of the method includes a first carriage and first track configured to maintain a continuous non-contact interface between the first sensor and the first scale, the first track should be affixed securely to the object (e.g., using a ratcheted tie down) prior to carrying out an inspection of the object.

Method Using Two-Axis Scanner System

Figure 10A:
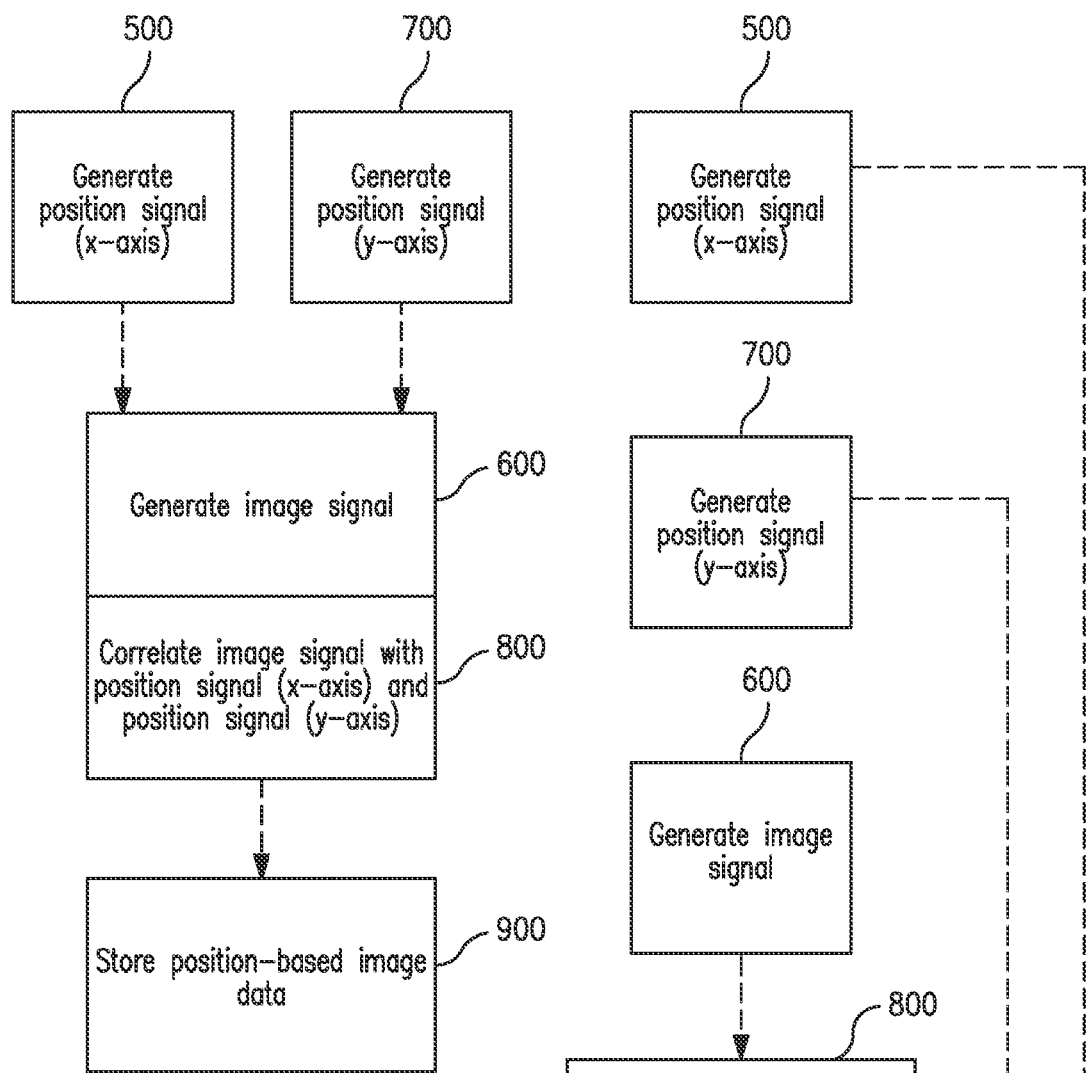
FIG. 10A is a flowchart of an embodiment of a method for image inspection of an object using an embodiment of the two-axis scanner system of FIG. 8.
Figure 10B:
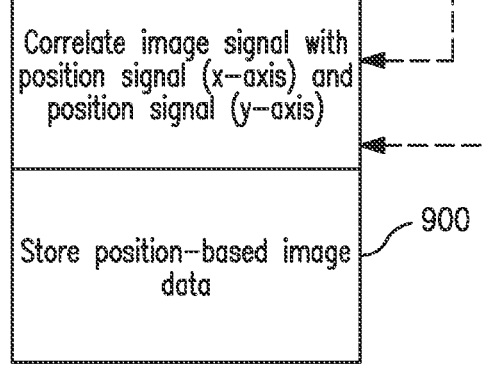
FIG. 10B is a flowchart of a second embodiment of the method for image inspection of an object using an embodiment of the two-axis scanner system of FIG. 8.

Embodiments of a method for image inspection of an object using a two-axis scanner system (e.g., a scanner system including an inspection probe and first and second non-contact linear encoders, the first non-contact linear encoder having a first sensor and a first scale and the second non-contact linear encoder having a second sensor and a second scale, the first sensor positioned to maintain a continuous non-contact interface between the first sensor and the first scale and to maintain a continuous alignment of the first sensor with the inspection probe and the second sensor positioned to maintain a continuous non-contact interface between the second sensor and the second scale and to maintain a continuous alignment of the second sensor with the first sensor, the continuous alignment of the second sensor and the first sensor being substantially perpendicular to the alignment of the first sensor and the inspection probe) include five operations 500, 600, 700, 800, 900 (as depicted in FIGS. 10A and 10B).

The first and second operations 500, 600 are substantially similar to the first and second operations, respectively, included in the embodiments of a method for image inspection of an object using the single-axis scanner system of FIGS. 9A and 9B. Specifically, the first operation 500 includes generating a signal representative of a position of the inspection probe on a first axis by having an operator move the first sensor along the first scale on the first axis x-axis). The second operation 600 includes generating a signal representative of an image of the object using the inspection probe.

The third operation 700 includes generating a signal representative of a position of the inspection probe on a second axis (i.e., y-axis). The third operation 700 may be carried out by connecting the second sensor to an appropriate power supply and ensuring that the second sensor is prepared to read the second scale. The second sensor may then be moved along the second scale on the second axis by an operator while a continuous non-contact interface is maintained between the second sensor and the second scale, such that the second sensor is able to read the second scale. The second axis is aligned perpendicular to the first axis to allow for the collection of two-dimensional (i.e., x-y plane) inspection probe position data.

The fourth operation 800 includes correlating the signal representative of a position of the inspection probe on a first axis (generated by the first sensor) with the signal representative of a position of the inspection probe on a second axis (generated by the second sensor) and the signal representative of an image of the object (generated by the inspection probe). The signal representative of a position of the inspection probe on a first axis and the signal representative of a position of the inspection probe on a second axis may be input directly into the inspection probe, as depicted in FIG. 10A, if the inspection probe is compatible with the signals. Alternatively, the signals may be input into a compute not shown) having appropriate software.

The fifth operation 900 includes storing position-based image data obtained from the previous four operations 500, 600, 700, 800 using the computer. The position-based image data stored on the computer may be displayed to an operator and/or analyzed for other purposes using appropriate software (e.g., comparing images taken of a single inspection location over time to track the development of cracks or a decrease in pipe wall thickness).

Embodiments of the method discussed herein allow an operator to acquire two-dimensional (i.e., x-y plane) inspection probe position data, thereby being advantageous as compared to related methods. This increases the feasibility of carrying out an inspection using a scanner system that uses a conventional ultrasonic inspection probe or eddy current inspection probe, which are only capable of scanning in a single direction from a fixed inspection point. When the two-axis scanner system used in an embodiment of the method includes a second carriage and second track configured to maintain a continuous non-contact interface between the second sensor and the second scale, the second track should be affixed securely to the object (e.g., using a ratcheted tie down) prior to carrying out an inspection of the object.

What is claimed is:

1. A scanner system for an image inspection of an object, the scanner system comprising:
   an inspection probe; and
   a first non-contact linear encoder, the first non-contact linear encoder comprising:
     a first scale, and
     a first sensor configured to read the first scale,
       wherein the first sensor is positioned to face the first scale and maintain a continuous non-contact interface between the first sensor and the first scale, and
       wherein the first sensor is configured to move with respect to the first scale;
   wherein the first sensor is associated with the inspection probe so that a continuous alignment between the first sensor and the inspection probe is maintained for a duration of the image inspection.

2. The scanner system according to claim 1, wherein the first non-contact linear encoder is a magnetic non-contact linear encoder or an optical non-contact linear encoder.

3. A scanner system for image inspection of an object, the scanner system comprising:
   an inspection probe;
   a first non-contact linear encoder comprising:
     a first sensor, and
     a first scale,
   the first sensor being positioned to maintain a continuous non-contact interface between the first sensor and the first scale and to maintain a continuous alignment of the first sensor with the inspection probe;
   a first track;
   a first carriage; and
   a probe mount, wherein:
   the first scale is affixed to the first track, the first sensor is affixed to the first carriage, and the first carriage is connected to and moveable along the first track to maintain the continuous non-contact interface between the first sensor and the first scale, and
   the probe mount is connected to the first carriage and connected to the inspection probe to maintain the continuous alignment of the first sensor with the inspection probe.

4. The scanner system according to claim 1, further comprising a second non-contact linear encoder, comprising:
   a second scale, and
   a second sensor configured to read the second scale,
     wherein the second sensor is positioned to face the second scale and maintain a continuous non-contact interface between the second sensor and the second scale, and
     wherein the second sensor is configured to move with respect to the second scale;
   wherein the second sensor is associated with the first sensor so that a continuous alignment between the second sensor and the first sensor is maintained for the duration of the image inspection.

5. The scanner system according to claim 1, wherein the inspection probe is a phased array ultrasonic inspection probe or a conventional ultrasonic inspection probe or an eddy current inspection probe.

6. The scanner system according to claim 3, wherein:
the object is a pipe having a longitudinal axis and a weld having a weld toe;
the first track is positioned on top of the weld; and
the probe mount extends a maximum distance of 2.125 inches from the weld toe along the longitudinal axis of the pipe.

7. The scanner system according to claim 3, further comprising:
first and second connecting members; and
first, second, and third grooves, wherein:
the first connecting member fits within the first groove and the second connecting member fits within the second groove to connect the first carriage to the first track, and
the first scale is positioned within the third groove.

8. The scanner system according to claim 4, wherein:
the first non-contact linear encoder is a magnetic non-contact linear encoder or an optical non-contact linear encoder; and
the second non-contact linear encoder is a magnetic non-contact linear encoder or an optical non-contact linear encoder.

9. The scanner system according to claim 3, further comprising:
a second track;
a second carriage; and
a second non-contact linear encoder, the second non-contact linear encoder comprising:
a second sensor, and
a second scale, wherein:
the second scale is affixed to the second track, the second sensor is affixed to the second carriage, and the second carriage is connected to and moveable along the second track to maintain a continuous non-contact interface between the second sensor and the second scale, and
the first track is affixed to the second carriage and aligned perpendicular to the second track to maintain an alignment of the second sensor with the first sensor.

10. The scanner system according to claim 3, wherein the probe mount comprises:
a probe mount base;
a probe mount pivot;
first and second probe mount links; and
first and second probe mount yokes, wherein:
the probe mount base is affixed to the first carriage,
the probe mount pivot is affixed to the probe mount base,
the first and second probe mount links are connected to the probe mount pivot,
the first probe mount yoke is connected to the first probe mount link,
the second probe mount yoke is connected to the second probe mount link, and
the first and second probe mount yokes are connected to the inspection probe.

11. The scanner system according to claim 9, wherein the probe mount comprises:
a probe mount base;
a probe mount pivot having a first side and a second side;
first and second probe mount links; and
first and second probe mount yokes, wherein:
the probe mount base is affixed to the first carriage,
the probe mount pivot is affixed to the probe mount base,
the first and second probe mount links are connected to the probe mount pivot,
the first probe mount yoke is connected to the first probe mount link,
the second probe mount yoke is connected to the second probe mount link, and
the first and second probe mount yokes are connected to the inspection probe.

12. The scanner system according to claim 9, further comprising:
first, second, third, and fourth connecting members; and
first, second, third, fourth, fifth, and sixth grooves, wherein:
the first connecting member fits within the first groove and the second connecting member fits within the second groove to connect the first carriage to the first track,
the third connecting member fits within the fourth groove and the fourth connecting member fits within the fifth groove to connect the second carriage to the second track,
the first scale is positioned within the third groove, and
the second scale is positioned within the sixth groove.

13. The scanner system according to claim 7, wherein:
the first track has first, second, and third surfaces,
the first carriage comprises:
a first right half carriage, and
a first left half carriage,
the first connecting member is located on the first right half carriage,
the second connecting member is located on the first left half carriage,
the first groove is located on the first surface,
the second groove is located on the second surface, and
the third groove is located on the third surface.

14. The scanner system according to claim 12, wherein:
the first track has first, second, and third surfaces,
the second track has fourth, fifth, and sixth surfaces,
the first carriage comprises:
a first right half carriage, and
a first left half carriage,
the second carriage comprises:
a second right half carriage, and
a second left half carriage,
the first connecting member is located on the first right half carriage,
the second connecting member is located on the first left half carriage,
the third connecting member is located on the second right half carriage,
the fourth connecting member is located on the second left half carriage,
the first groove is located on the first surface,
the second groove is located on the second surface,
the third groove is located on the third surface,
the fourth groove is located on the fourth surface,
the fifth groove is located on the fifth surface, and
the sixth groove is located on the sixth surface.

15. A method for image inspection of an object using a scanner system having an inspection probe and a first non-contact linear encoder having a first sensor facing and configured to read a first scale, the method comprising:
moving the inspection probe on the object; and
generating a signal representative of a position of the inspection probe on the object by moving the first sensor along the first scale while
maintaining a continuous non-contact interface between the first sensor and the first scale and maintaining a continuous alignment of the first sensor with the inspection probe while the first sensor is moving along the first scale and the inspection probe is moving on the object.

16. A method for image inspection of an object using a scanner system having an inspection probe and first and second non-contact linear encoders, the first non-contact linear encoder having a first sensor and a first scale and the second non-contact linear encoder having a second sensor and a second scale, the method comprising:
generating a signal representative of a position of the inspection probe on a first axis by moving the first sensor along the first scale on the first axis while maintaining a continuous non-contact interface between the first sensor and the first scale and maintaining a continuous alignment of the first sensor with the inspection probe; and
generating a signal representative of a position of the inspection probe on a second axis by moving the second sensor along the second scale on the second axis while maintaining a continuous non-contact interface between the second sensor and the second scale and maintaining a continuous alignment of the second sensor with the first sensor.

17. The scanner system according to claim 1, further comprising:
a first track;
a first carriage; and
a probe mount, wherein:
the first scale is affixed to the first track, the first sensor is affixed to the first carriage, and the first carriage is connected to and moveable along the first track to maintain the continuous non-contact interface between the first sensor and the first scale, and
the probe mount is connected to the first carriage and connected to the inspection probe to maintain the continuous alignment of the first sensor with the inspection probe.

18. The scanner system according to claim 17, wherein:
the object is a pipe having a longitudinal axis and a weld having a weld toe;
the first track is positioned on top of the weld; and
the probe mount extends a maximum distance of 2.125 inches from the weld toe along the longitudinal axis of the pipe.

19. The scanner system according to claim 17, further comprising:
first and second connecting members; and
first, second, and third grooves, wherein:
the first connecting member fits within the first groove and the second connecting member fits within the second groove to connect the first carriage to the first track, and
the first scale is positioned within the third groove.

20. The scanner system according to claim 19, wherein:
the first non-contact linear encoder is a magnetic non-contact linear encoder or an optical non-contact linear encoder; and
a second non-contact linear encoder is a magnetic non-contact linear encoder or an optical non-contact linear encoder.

* * * * *